(12) United States Patent
Bhalay et al.

(10) Patent No.: US 7,259,173 B2
(45) Date of Patent: Aug. 21, 2007

(54) DERIVATIVES OF 3-PHENYL-N-(2-(4-BENZYL)-PIPERIDIN-1-YL)-ETHYL)-ACRYLAMID WITH CCR-3-RECEPTOR ANTAGONISTIC ACTIVITY FOR USE IN THE TREATMENT OF INFLAMMATIONS AND ALLERGIC CONDITIONS

(75) Inventors: Gurdip Bhalay, Horsham (GB); Clive Victor Walker, Horsham (GB)

(73) Assignee: Novartis AG, Basel (CH)

( * ) Notice: Subject to any disclaimer, the term of this patent is extended or adjusted under 35 U.S.C. 154(b) by 547 days.

(21) Appl. No.: 10/478,795

(22) PCT Filed: Jun. 14, 2002

(86) PCT No.: PCT/EP02/06588

§ 371 (c)(1),
(2), (4) Date: Apr. 23, 2004

(87) PCT Pub. No.: WO02/102775

PCT Pub. Date: Dec. 27, 2002

(65) Prior Publication Data

US 2004/0180926 A1 Sep. 16, 2004

(30) Foreign Application Priority Data

Jun. 15, 2001 (GB) ................... 0114699.2

(51) Int. Cl.
| A61K 31/445 | (2006.01) |
| C07D 211/14 | (2006.01) |
| C07D 211/18 | (2006.01) |
| C07D 211/48 | (2006.01) |

(52) U.S. Cl. .............. 514/327; 514/331; 546/221; 546/230; 546/234

(58) Field of Classification Search ........... 546/221, 546/230, 234; 514/327, 331
See application file for complete search history.

(56) References Cited

FOREIGN PATENT DOCUMENTS

| EP | 0 226 516 | 6/1987 |
| EP | 0 903 349 | 3/1999 |
| WO | 00/29377 | 5/2000 |
| WO | 00/31033 | 6/2000 |
| WO | 00/58305 | 10/2000 |
| WO | 02/04420 | 1/2002 |

*Primary Examiner*—Bernard Dentz
(74) *Attorney, Agent, or Firm*—Gregory C. Houghton

(57) ABSTRACT

This invention relates to organic compounds of formula I,

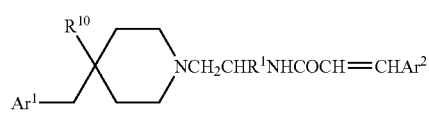

in which $Ar^1$ is unsubstituted phenyl substituted by one or more halogen atoms; $Ar^2$ is unsubstituted phenyl or phenyl substituted by one or more substituents selected from the group consisting of halogen, cyano and $C_1$-$C_8$-alkoxy; $R^1$ is hydrogen or methyl optionally substituted by hydroxy; $R^{10}$ is hydrogen or hydroxy; and pharmaceutically acceptable salts thereof. Compositions containing them, methods for their preparation and their use as pharmaceuticals are also described.

14 Claims, No Drawings

DERIVATIVES OF 3-PHENYL-N-(2-(4-BENZYL)-PIPERIDIN-1-YL)-ETHYL)-ACRYLAMID WITH CCR-3-RECEPTOR ANTAGONISTIC ACTIVITY FOR USE IN THE TREATMENT OF INFLAMMATIONS AND ALLERGIC CONDITIONS

This invention relates to organic compounds, compositions containing them, methods for their preparation and their use as pharmaceuticals.

In one aspect, the invention provides compounds of formula I,

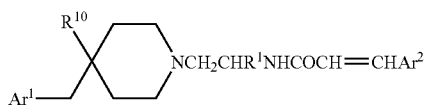

in which

Ar$^1$ is unsubstituted phenyl or phenyl substituted by one or more halogen atoms;

Ar$^2$ is unsubstituted phenyl or phenyl substituted by one or more substituents selected from halogen, cyano or $C_1$-$C_8$-alkoxy;

R$^1$ is hydrogen or methyl optionally substituted by hydroxy;

R$^{10}$ is hydrogen or hydroxy;

and pharmaceutically acceptable salts thereof.

Terms used in the specification have the following meanings:

"$C_1$-$C_8$-alkoxy" as used herein denotes straight chain or branched $C_1$-$C_8$-alkoxy which may be, for example, methoxy, ethoxy, n-propoxy, isopropoxy, n-butoxy, isobutoxy, sec-butoxy, tert-butoxy, straight or branched pentoxy, straight or branched hexyloxy, straight or branched heptyloxy, or straight or branched octyloxy. Preferably, $C_1$-$C_8$-alkoxy is $C_1$-$C_4$-alkoxy.

"Halogen" as used herein may be fluorine, chlorine, bromine or iodine; preferably it is fluorine, chlorine or bromine.

In Ar$^1$, the phenyl group may be substituted by one, two or three, preferably one or two halogen atoms, preferably selected from fluorine and chlorine atoms. When there is one halogen substituent, it is preferably para to the indicated methylene group. When there are two or three halogen substituents, preferably one is para to the indicated methylene group and at least one of the others is ortho to the indicated methylene group.

Ar$^2$ as substituted phenyl may for example, be substituted by one, two, three, four or five, preferably by one, two or three, of the above-mentioned substituents. Ar$^2$ may be for example, monosubstituted phenyl in which the substituent, preferably halogen, cyano or $C_1$-$C_4$-alkoxy, is preferably ortho or meta to the indicated —CH═CH— group. Ar$^2$ may alternatively be, for example, disubstituted phenyl in which the substituents are especially two halogen substituents (same or different halogen), two $C_1$-$C_4$-alkoxy groups, one halogen and one cyano, one halogen and one $C_1$-$C_4$-alkoxy, or one cyano and one $C_1$-$C_4$-alkoxy. Ar$^2$ may alternatively be, for example, trisubstituted phenyl in which the substituents are preferably selected from halogen and $C_1$-$C_4$-alkoxy, especially three halogen substituents (same or two or three different halogens), or two $C_1$-$C_4$-alkoxy and one halogen.

Ar$^2$ may alternatively be, for example, penta-substituted phenyl in which the substituents are preferably halogen, especially fluorine. Especially preferred groups Ar$^2$ are cyanophenyl, particularly meta-cyanophenyl, and disubstituted phenyl where one substituent is $C_1$-$C_4$-alkoxy, preferably ortho to the CH═CH— group, and the other, preferably para to the $C_1$-$C_4$-alkoxy group, is $C_1$-$C_4$-alkoxy, halogen or cyano.

Preferred compounds of formula I or salts thereof include those in which Ar$^1$ is phenyl substituted by fluorine or chlorine para to the indicated methylene group.

Pharmaceutically acceptable acid addition salts of the compounds of formula I include those of inorganic acid, for example, hydrohalic acids such as hydrofluoric acid, hydrochloric acid, hydrobromic acid or hydroiodic acid, nitric acid, sulfuric acid, phosphoric acid; and organic acids, for example, aliphatic monocarboxylic acid such as formic acid, acetic acid, trifluoroacetic acid, propionic acid and butyric acid, aliphatic hydroxy acid such as lactic acid citric acid, tartaric acid or malic acid, dicarboxylic acid such as maleic acid or succinic acid, aromatic carboxylic acid such as benzoic acid, p-chlorobenzoic acid, diphenylacetic acid or triphenylacetic acid, aromatic hydroxy acids such as ohydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Certain carbon atoms in the compounds of formula I may be asymmetric, for example when R$^1$ is other than hydrogen. These compounds may thus exist in individual optically active isomeric forms or as mixtures thereof, e.g., a racemic or diastereomeric mixtures. The invention embraces both individually optically active R and S isomers as well as mixtures, e.g., racemic or diastereomeric mixtures, thereof. Racemic mixtures may be separated into enantiomers by conventional methods known per se.

The invention also provides a process for the preparation of compounds of formula I which comprises:

(i) (A) for the preparation of compounds of formula I wherein R$^{10}$ represents OH, reacting a compound of formula II

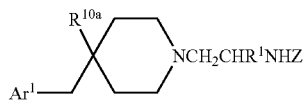

where Ar$^1$ and R$^1$ are as defined above, R$^{10a}$ represents OH and Z denotes a solid phase substrate chemically linked to the indicated nitrogen atom with a compound of formula III

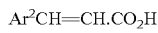

or an amide forming derivative thereof, in which Ar$^2$ is as defined above, and detaching the resulting product from the substrate to replace Z by hydrogen; or (B) for the preparation of compounds of formula I wherein R$^{10}$ represents hydrogen, reacting a compound of formula IV

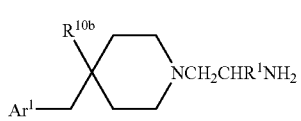

IV where Ar$^1$, Ar$^2$ and R$^1$ are as defined above and R$^{10b}$ represents hydrogen, with a compound of formula III, as defined above or an amide forming derivative thereof, and (ii) where desired or necessary, converting the resulting salt into the compound of formula I or vice versa.

Process variant A may be carried out using known methods, for example by reacting the substrate-bound compound with the free acid under known peptide coupling conditions, for example in the presence of a tertiary amine and a peptide coupling agent such as those mentioned above, or analogously, e.g. as hereinafter described in the Examples. The reaction may be carried out in an organic solvent inert to the reaction conditions, as dimethylformamide (DMF). Suitable reaction temperatures are from 0 to 40° C., e.g. 15 to 25° C. The reaction product may be detached from the substrate in a known manner, for example, where the N atom is linked to a CH$_2$ of a benzyl group in Z, by treatment with trifluoroacetic acid.

Process variant B may be carried out using known methods, for example by reacting a compound of formula IV with an acid halide, particularly an acid chloride, of the acid of formula III using known amide-forming procedures, or analogously, e.g. as hereinafter described in the Examples. Alternatively, the compound of formula IV may be reacted with a free carboxylic acid of formula III, using for example, known procedures, such as reacting in the presence of a tertiary amine and a peptide coupling agent such as a phosphonium salt, 2-(1H-benzotriazol-1-yl)-1,1,3,3-tetramethyl uronium tetrafluorobenzate or diisopropylcarbodiimide; this reaction may be carried out in an organic solvent inert to the reaction conditions, for example a halohydrocarbon such as dichloromethane, the reaction temperature is conveniently from 0 to 40° C., preferably ambient temperature.

Compounds of formula III are either available commercially or may be prepared by conventional methods known per se.

Compounds of formula II, in which R$^1$ represents hydrogen and R$^{10a}$ represents —OH may be prepared in accordance with Scheme A (Process A in combination with Scheme A is hereinafter referred to as Method A):

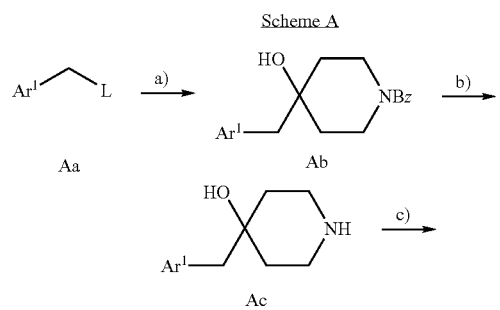

in which in step a), the compound of formula Aa, in which L is a leaving group, e.g. chloride, and Ar$^1$ is as defined above, is reacted with magnesium turnings, under Grignard conditions to form a Grignard agent which is reacted in situ with 1-benzyl-piperidin4-one, which on work up gives the compound of formula Ab;

in step b) the benzyl protecting group of the compound of formula Ab is removed by hydrogenation, e.g. using H$_2$/Pd-charcoal to give the compound of formula Ac;

in step c) the compound of formula II above in which R$^{10}$ represents hydrogen, R$^{10}$ represents OH and Ar$^2$ and Z are as defined above, may be prepared using a protected 2-haloethylene derivative, using the conditions described in Example 1.

Compounds of formula Aa are either known, or may be made by conventional techniques, known per se.

Compounds of formula IV, in which R$^1$ represents —CH$_2$OH may be prepared in accordance with Scheme B(Process B in combination with Scheme B is hereinafter referred to as Method B):

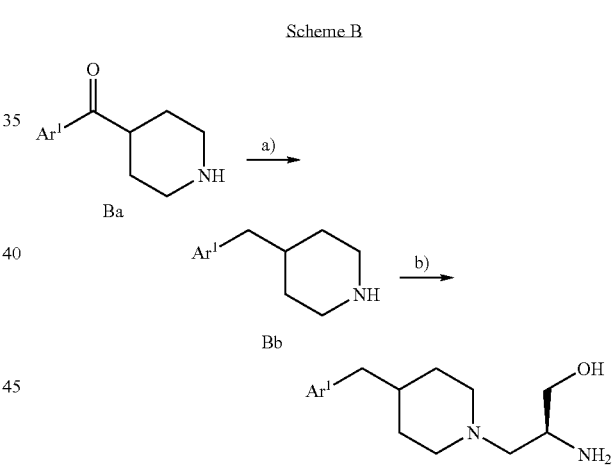

in which in step a), the compound of formula Ba is reduced to the compound of formula B1b using a selective reducing agent, e.g. a hydride reducing agent such as triethylsilyl hydride in trifluoromethanesulfonic acid;.

in step b), the compound of formula IV, in which R$^1$ represents —CH$_2$OH may be prepared by reacting Bb with the Garner aldehyde, (R)-4-formyl-2,2-dimethyl-oxazolidine-3-carboxylic acid tert-butyl ester.

Specific conditions and reagents for steps a) and b) are exemplified in Example 2.

Compounds of formula Ba are either known or may be made by conventional methods known per se.

Compounds of formula IV, in which R$^1$ is hydrogen may be prepared in accordance with Scheme C (Process B in combination with Scheme C is hereinafter referred to as Method C):

Scheme C

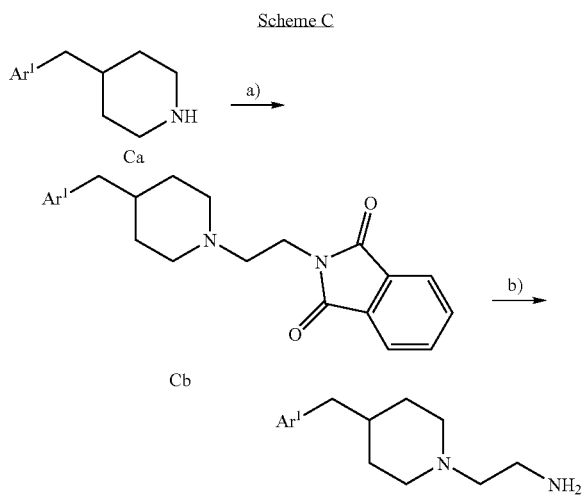

in which in step a), the compound of formula Cb in which Ar$^1$ is as defined above, may be prepared by reacting a corresponding compound of formula Ca with 2-(2-bromoethyl)-isoindole-1,3dione in the presence of a base, e.g. trimethylamine, in an inert solvent;

in step b), the compound of formula IV, in which R$^1$ and R$^{10}$ are each hydrogen and Ar$^1$ is as defined above may be prepared by cleavage of the compound of formula Cb with hydrazine.

Specific conditions and reagents for steps a) and b) are exemplified in Example 3.

Compounds of formula Ca are either known or may be made by the method described for compounds of formula Bb described in Scheme B above.

Compounds of formula II, in which R$^1$ represents methyl or —CH$_2$OH may be prepared using the method of Scheme B and the intermediate Ac of Scheme A.

Compounds of formula I may be converted into pharmaceutically acceptable salt thereof, or vice versa, in a conventional manner. The compounds of formula I and their pharmaceutically acceptable salts can be obtained in the form of hydrates or solvates containing a solvent used for crystallisation. Compounds of formula I, and salts thereof, can be recovered from reaction mixtures and purified in a conventional manner. Isomers, such as enantiomers, may be obtained in a conventional manner, e.g. by fractional crystallisation or asymmetric synthesis from correspondingly asymmetrically substituted, e.g. optically active, starting materials.

Compounds of formula I and pharmaceutically acceptable salts thereof, hereinafter referred to alternatively as agents of the invention, are useful as pharmaceuticals. Accordingly the invention also provides a compound of formula I, or a pharmaceutically acceptable salt thereof, for use as a pharmaceutical. The agents of the invention act as CCR-3 receptor antagonists, thereby inhibiting the infiltration and activation of inflammatory cells, particularly eosinophils, and inhibiting allergic response. The inhibitory properties of agents of the invention can be demonstrated in the following assay:

CCR-3 Binding Assay

In this assay the effect of agents of the invention on the binding of human eotaxin to human CCR-3 is determined. Recombinant cells expressing human CCR-3 are captured by wheatgerm agglutinin (WGA) polyvinyltoluidene (PVT) SPA beads (available from Amersham), through a specific interaction between the WGA and carbohydrate residues of glycoproteins on the surface of the cells. [$^{125}$I]-human eotaxin (available from Amersham) binds specifically to CCR-3 receptors bringing the [$^{125}$I]-human eotaxin in close proximity to the SPA beads. Emitted â-particles from the [$^{125}$I]-human eotaxin excite, by its proximity, the fluorophore in the beads and produce light. Free [$^{125}$I]-human eotaxin in solution is not in close proximity to the scintillant and hence does not produce light. The scintillation count is therefore a measure of the extent to which the test compound inhibits binding of the eotaxin to the CCR-3.

Preparation of Assay Buffer: 5.96 g HEPES and 7.0 g sodium chloride are dissolved in distilled water and 1M aqueous CaCl$_2$ (1 mL) and 1M aqueous MgCl$_2$ (5 mL) are added. The pH is adjusted to 7.6 with NaOH and the solution made to a final volume of 1 L using distilled water. 5 g bovine serum albumin and 0.1 g sodium azide are then dissolved in the solution and the resulting buffer stored at 4° C. A Complete™ protease inhibitor cocktail tablet (available from Boehringer) is added per 50 mL of the buffer on the day of use.

Preparation of Homogenisation Buffer: Tris-base (2.42 g) is dissolved in distilled water, the pH of the solution is adjusted to 7.6 with hydrochloric acid and the solution is diluted with distilled water to a final volume of 1 L. The resulting buffer is stored at 4° C. A Complete™ protease inhibitor cocktail tablet is added per 50 mL of the buffer on the day of use.

Preparation of membranes: Confluent rat basophil leukemia (RBL-2H3) cells stably expressing CCR3 are removed from tissue culture flasks using enzyme-free cell dissociation buffer and resuspended in phosphate-buffered saline. The cells are centrifuged (800 g, 5 minutes), the pellet resuspended in ice-cold homogenisation buffer using 1 mL homogenisation buffer per gram of cells and incubated on ice for 30 minutes. The cells are homogenised on ice with 10 strokes in a glass mortar and pestle. The homogenate is centrifuged (800 g, 5 minutes, 4° C.), the supernatant further centrifuged (48,000 g, 30 minutes, 4° C.) and the pellet redissolved in Homogenisation Buffer containing 10% (v/v) glycerol. The protein content of the membrane preparation is estimated by the method of Bradford (Anal. Biochem. (1976) 72:248) and aliquots are snap frozen and stored at −80° C.

The assay is performed in a final volume of 250 μL per well of an Optiplate (ex Canberra Packard). To selected wells of the Optiplate are added 50 μL of solutions of a test compound in Assay Buffer containing 5% DMSO (concentrations from 0.1 nM to 10 μM). To determine total binding, 50 μL of the Assay Buffer containing 5% DMSO is added to other selected wells. To determine non-specific binding, 50 μL of 100 nM human eotaxin (ex R&D Systems) in Assay Buffer containing 5% DMSO is added to further selected wells. To all wells are added 50 μL [$^{125}$I]-Human eotaxin (ex Amersham) in Assay Buffer containing 5% DMSO at a concentration of 250 pM (to give a final concentration of 50 pM per well), 50 μL of WGA-PVT SPA beads in Assay Buffer (to give a final concentration of 1.0 mg beads per well) and 100 μL of the membrane preparation at a concentration of 100 μg protein in Assay Buffer (to give a final concentration of 10 μg protein per well). The plate is then incubated for 4 hours at room temperature. The plate is sealed using TopSeal-S (ex Canberra Packard) according to the manufacturer's instructions. The resulting scintillations are counted using a Canberra Packard TopCount, each well being counted for 1 minute. The concentration of test compound at which 50% inhibition occurs (ICso) is determined from concentration-inhibition curves in a conventional manner.

The compounds of the Examples hereinbelow have $IC_{50}$ values of the order of 1 µM or less in the above assay. For instance, the compounds of Examples 2, 3, 4 and 6 have $IC_{50}$ values of 6 nM, 34.7 nM, 6 nM and 51.8 nM respectively.

Having regard to their inhibition of binding of CCR-3, agents of the invention are useful in the treatment of conditions mediated by CCR-3,particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, diseases of the bone or joints including rheumatoid arthritis, inflammatory conditions of the gastrointestinal tract, for example inflammatory bowel disease such as ulcerative colitis and Crohn's disease and other diseases such as atherosclerosis, multiple sclerosis and diabetes.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, J. Immunol. Methods (1997) 202:49-57; Renzi et al, Am. Rev. Respir. Dis. (1993) 148:932-939; Tsuyuki et al., J. Clin. Invest. (1995) 96:2924-2931; and Cernadas et al (1999) Am. J. Respir. Cell Mol. Biol. 20:1-8.

The agents of the invention are also useful as co-therapeutic agents for use in conjunction with anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the anti-inflammatory or bronchodilatory drug in a fixed pharmaceutical composition or it may be administered separately, before, simultaneously with or after the anti-inflammatory or bronchodilatory drug. Such anti-inflammatory drugs include steroids, in particular glucocorticosteroids such as budesonide, beclamethasone, fluticasone or mometasone, LTB4 antagonists such as those described in U.S. Pat. No. 5,451,700, LTD4 antagonists such as montelukast and zafirlukast, and PDE4 inhibitors such as Ariflo® (GlaxoSmith Kline), Roflumilast (Byk Gulden),V-11294A (Napp), BAY19-8004 (Bayer), SCH-351591 (Schering-Plough), and PD189659 (Parke-Davis). Such bronchodilatory drugs include anticholinergic or antimuscarinic agents, in particular ipratropium bromide, oxitropium bromide and tiotropium bromide, and beta-2 adrenoceptor agonists such as salbutamol, terbutaline, salmeterol and, especially, formoterol and pharmaceutically acceptable salts thereof, and compounds (in free or salt or solvate form) of formula I of PCT International Publication No. WO00/75114,which document is incorporated herein by reference, preferably compounds of the Examples thereof, especially a compound of formula

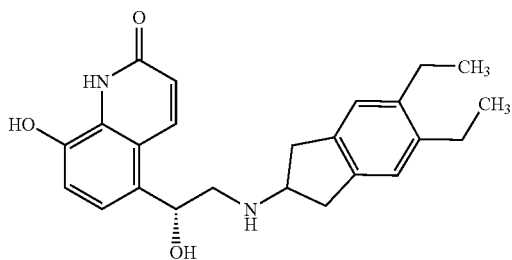

and pharmaceutically acceptable salts thereof. Co-therapeutic antihistamine drug substances include cetirizine hydrochloride, acetarninophen, clemastine fumarate, promethazine, loratidine, desloratidine, diphenhydramine and fexofenadine hydrochloride. Combinations of agents of the invention and steroids, beta-2 agonists, PDE4 inhibitors or LTD4 antagonists may be used, for example, in the treatment of COPD or, particularly, asthma. Combinations of agents of the invention and anticholinergic or antimuscarinic agents, PDE4 inhibitors or LTB4 antagonists may be used, for example, in the treatment of asthma or, particularly, COPD.

In accordance with the foregoing, the invention also provides a method for the treatment of a condition mediated by CCR-3,for example an inflammatory or allergic condition, particularly an inflammatory or obstructive airways disease, which comprises administering to a subject, particularly a human subject, in need thereof an effective amount of a compound of formula I in a free or pharmaceutically acceptable salt form as hereinbefore described. In another aspect the invention provides the use of a compound of formula I, in free or pharmaceutically acceptable salt form, as hereinbefore described for the manufacture of a medicament for the treatment of a condition mediated by CCR-3,for example an inflammatory or allergic condition, particularly an inflammatory or obstructive airways disease.

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

In a further aspect, the invention also provides a pharmaceutical composition comprising as active ingredient a compound of formula I in free or pharmaceutically acceptable salt form, optionally together with a pharmaceutically acceptable diluent or carrier therefor. The composition may contain a co-therapeutic agent such as an anti-inflammatory or bronchodilatory drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

The invention includes (A) an agent of the invention in inhalable form, e.g. in an aerosol or other atomisable composition or in inhalable particulate, e.g. micronised form, (B) an inhalable medicament comprising an agent of the invention in inhalable form; (C) a pharmaceutical product comprising such an agent of the invention in inhalable form in association with an inhalation device; and (D) an inhalation device containing an agent of the invention in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.01 to 30 mg/kg while for oral administration suitable daily doses are of the order of 0.01 to 100 mg/kg.

EXAMPLE 1

Method A (E)-3-(5-Bromo-2-methoxy-phenyl)-N-{2-[4-(4-fluoro-benzyl)-4-hydroxy-piperidin-1-yl]-ethyl}-acrylamide 1-Benzyl-4-(4-fluoro-benzyl)-piperidin-4-ol To a suspension of magnesium metal (4.15 g, 170.5 mmol) in anhydrous THF (40 ml) is added 1,2-dibromoethane (1.53 g, 8.12 mmol) and the mixture warmed gently. To the reaction mixture is added a solution of 1-chloromethyl-4-fluoro-benzene (23.5 g, 162.4 mmol) in THF (20 ml) dropwise over 1.5 hours. The reaction mixture is cooled to RT and stirred for 0.5 hours followed by cooling to −10° C. and addition of a solution of 1-benzyl-piperidin-4-one (9.19 g, 48.6 mmol) in THF (20 ml) dropwise over 0.5 hours. During the addition the reaction temperature is maintained below 0° C. After addition is complete the reaction is allowed to reach RT and stirred for 4 days. The resultant suspension is cooled in ice, treated with saturated ammonium chloride, stirred for 0.3 hours, treated with water and the mixture extracted with ethyl acetate. The ethyl acetate is dried with magnesium sulphate and evaporated. The crude product is purified by flash silica chromatography (methanol:dichloromethane: anmuoniumhydroxide, 1:100:0.5 elution) to afford 1-benzyl-4-(4-fluoro-benzyl)-piperidin-4-ol [MH]$^+$ 300.8

4-(4-fluoro-benzyl)-piperidin-4-ol acetate

A solution of 1-benzyl-4-(4-fluoro-benzyl)-piperidin-4-ol (5.87 g, 19.6 mmol) in ethanol (80 ml) is treated with acetic acid (1 ml) and with 10% Pd on carbon (1 g). The mixture is stirred at RT under an atmosphere of hydrogen for 20 hours. The mixtre is filtered and the filtrate evaporated. The crude product is treated with dichloromethane. The resultant suspension is filtered and the white solid obtained is washed with cold dichloromethane to afford 4-(4-fluoro-benzyl)-piperidin-4-ol acetate [MH]$^+$ 210.1

(E)-3-(5-Bromo-2-methoxyphenyl)-N-{2-[4-(4-fluoro-benzyl)-4-hydroxy-piperidin-1-yl]-ethyl}-acrylamide To a suspension of 2-(formyl-3-methoxyphenoxy)ethyl polystyrene (AMEBA) resin (ex Novabiochem) (1.5 g, 1.05 mmol) in a mixture of trimethylorthoformate/dichloromethane (15 ml, 1:1 v/v) is added 2-amino ethanol (0.317 ml, 5.25 mmol), sodium triacetoxyborohydride (1.113 g, 5.25 mmol) followed by methanol (2 ml) and the mixture shaken for 8 hours at 20° C., then filtered. The resin is washed with methanol, dichloromethane and THF. The dried resin is suspended in THF/acetonitrile (40 ml, 9:1 v/v) and treated with triphenylphosphine (2.75 g, 10.5 mmol), imidazole (0.715 g, 10.5 mmol) and iodine (2.66 g, 10.5 mmol). The suspension obtained is, shaken for 6 hours at 20° C., then filtered. The resin is washed with THF followed by DMF and dried under vacuum. To the freshly prepared resin (1.0 g, 0.7 mmol) suspended in DMF (3 ml) is added 4-(4-fluoro-benzyl)-piperidin-4-ol acetate (0.399 g, 1.4 mmol) and diisopropylethylamine (0.36 g, 2.8 mmol). The mixture is heated at 50° C. for 16 hours and then filtered. The resin is washed with DMF. To the washed resin (0.5 g, 0.35 mmol ) suspended in DMF (3 ml) is added a solution of (E)-3-(5-bromo-2-methoxy-phenyl)-acrylic acid (0.27 g, 1.05 mmol), 2-(1H-benzotriazol-1-yl)-1,1,3,3,-tetramethyluronium tetrafluoroborate (0.34 g, 1.05 mmol), diisopropylethylamine (0.29 g, 1.05 mmol) in DMF (2 ml) and the mixture is shaken at 20° C. for 4 hours, then washed with DMF, methanol and dichloromethane after which it is treated with trifluoroacetic acid/dichloromethane (6 ml, 1:1 v/v) at 20° C. for 1 hour to remove the product from the resin. The resulting mixture is filtered and the filtrate evaporated under vacuum to give the crude product which is purified by preparative HPLC to afford (E)-3-(5-Bromo-2-methoxy-phenyl)-N-{2-[4-(4-fluoro-benzyl)-4-hydroxy-piperidin-1-yl]-ethyl}-acrylamide, as the trifluoroacetate salt, [MH]+ 490.9, 492.8

EXAMPLE 2

Method B (E3-(5-Cyano-2-methoxy-phenyl)-N-{(S)-2-[4-(4-chloro-benzyl)-piperidin-1-yl]-1-hydroxymethyl-ethyl}-acrylamide 4-(4-Chloro-benzyl)-piperidine A cooled (0-5° C.) solution of (4-chloro-phenyl)-piperidin4-yl-methanone (1.0 g, 4.47 mmol) in dichloromethane (20 ml) is treated with a solution of trifluoro-methanesulfonic acid (0.79 ml, 8.94 mmol) in dichloromethane (10 ml) followed by triethylsilane (1.07 ml, 6.7 mmol) in dichloromethane (5 ml), dropwise, whilst maintaining the reaction temperature at 0-5° C. The reaction is stirred for 5 minutes and more trifluoro-methanesulfonic acid (0.79 ml, 8.94 mmol) and triethylsilane (1.07 ml, 6.7 mmol) added. The resultant solution is stirred at room temperature for 2 hours and poured slowly onto cold saturated aqueous sodium bicarbonate (100 ml). The mixture is extracted with dichloromethane which is dried with magnesium sulphate and evaporated to afford the crude product. Any liquid present is decanted and the remaining solid co-evaporated with toluene. The crude semi-crystalline product is purified by flash silica chromatography (ethyl acetate elution followed by methanol:ethylacetate, 1:4 elution) to afford 4-(4 hloro-benzyl)-piperidine [MH]+ 210.0

(S)-4-[4-(4-chloro-benzl)-piperidin-1-ylmethyl]-2,2-dimethyl-oxazolidine-3-carboxylic acid .tert.-butyl ester A solution of (R)-4-formyl-2,2-dimethyl-oxazolidine-3-carboxylic acid .tert.-butyl ester (0.273 g, 1.19 mmol) in THF (5 ml) is treated with a solution of 4-(4-chloro-benzyl)-piperidine (0.25 g, 1.19 mmol) in THF (5 ml) followed by sodium triacetoxyborohydride (0.379 g, 1.79 mmol). The suspension is stirred at RT for 1.5 hours and evaporated. The crude residue is dissolved in ethyl acetate which is washed with aqueous sodium bicarbonate, brine and then dried with magnesium sulphate and evaporated to afford (S)-4-[4-(4-fluoro-benzyl)-piperidin-1-ylmethyl]-2,2dimethyl-oxazoldine-3-carboxylic acid .tert.-butyl ester [MH]+ 422.9

(S)-2-Amino-3-[4-(4-chloro-benzyl)-piperidin-1-yl]-propan-1-ol

A solution of (S)-4-[4-(4-chloro-benzyl)-piperidin-1-ylmethyl]-2,2-dimethyl-oxazolidine-3-carboxylic acid .tert.-butyl ester in HCl-dioxane (4M, 4 ml) is stirred at RT for 1 hour. The solution is evaporated and the crude residue azeotroped and evaporated from toluene to afford (S)-2-amino-3-[4-(4-fluoro-benzyl)-piperidin-1-yl]-propan-1-ol which is used directly [MH]+ 283.0

(E)-3-(5-Cyano-2-methoxy-phenyl)-N-{(S)-2-[4-(4-chloro-benzyl)-piperidin-1-yl]-1-hydroxymethyl-ethyl}-acrylamide A solution of (E)-3-(5-cyano-2-methoxy-phenyl)-acrylic acid (0.086 g, 0.42 mmol) in DMF (2 ml) was treated with diisopropylethylarine (0.082 g, 0.63 mmol) and with [dimethylamino-([1,2,3]triazolo[4,5-.b.]pyridin-3-yloxy)-methylene]-dimethyl-ammonium hexafluorophosphate (HATU) (0.24 g, 0.63 mmol). The solution is stirred for 0.5 hours at RT and treated with a solution of (S)-2-amino-3-[4-(4-fluoro-benzyl)-piperidin-1-yl]-propan-1-ol (0.15 g, 0.42 mmol) in DMF (1.5 ml). The reaction is stirred for 3.5 hours at RT. The solvent is evaporated and the crude mixture dissolved in ethyl acetate which is washed with aqueous sodium bicarbonate and brine. The ethyl acetate phase is dried with magnesium sulphate and evaporated. The crude product is purified by flash silica chromatography (ethyl acetate elution followed by methanol:ethylacetate, 1:4 elution ) to afford (E)-3-(5-cyano-2-methoxy-phenyl)-N-{(S)-2-[4-(4-chloro-benzyl)-piperidin-1-yl]-1-hydroxymethyl-ethyl}-acrylamide [MH]+ 468.3

EXAMPLE 3

Method C (E)-3-(5-Bromo-2-methoxy-phenyl)-N-{2-[4-(4-fluoro-benzyl)-piperidin-1-yl]-ethyl}-acrylamide 4-(4-Fluoro-benzyl)-piperidine 4-(4-fluoro-benzyl)-piperidine is prepared analogously to 4-(4-chloro-benzyl)-piperidine in Method B 2-{2-[4-(4-Fluoro-benzyl)-piperidin-1-yl]-ethyl}-isoindole-1,3-dione A solution of 4-(4-fluoro-benzyl)-piperidine (0.117 g, 0.6 mmol) in acetonitrile (5 ml) is treated with 2-(2-bromo-ethyl)-isoindole-1,3-dione (0.152 g, 0.6 mmol) and with triethylamine (0.084 ml, 0.6 mmol). The mixture is shaken at RT for 72 hours and the solvent evaporated. The crude product is purified by flash silica chromatography (methanol:dichloromethane, 1:19 elution) to afford 2-{2-[4-(4-fluoro-benzyl)-piperidin-1-yl]-ethyl}-isoindole-1,3-dione
$^1$H NMR (400 MHz, CDCl$_3$, selected values) δ 2.46 (d J 7.1 2H ), 2.60 (t J 6.8 2H ), 3.81 (t J 6.8 2H ), 6.94 (m 2H ), 7.05 (m 2H), 7.7 (dd J 3.0 5.3 2H), 7.84 (dd J 3.0 5.3 2H)

2-[-(4-Fluoro-benzyl)-piperidin-1-yl]-ethylamine

A solution of 2-{2-[4-(4-fluoro-benzyl)-piperidin-1-yl]-ethyl}-isoindole-1,3-dione (0.087 g, 0.24 mmol) in ethanol (20 ml) is treated with hydrazine hydrate (1.0 ml, 2 mmol) and heated under reflux for 1.5 hours. Most of the solvent is evaporated and the resultant solution is ice cooled for 0.5 hours. The precipitate is filtered off and the filtrate is evaporated to afford 2-[4-(4-fluoro-benzyl)-piperidin-1-yl]-ethylamine which is used directly, without further characterisation, in the next step.

(E)-3-(5-Bromo-2-methoxy-phenyl)-N-{2-[4-(4-fluoro-benzyl)-piperidin-1-yl]-ethyl}-acrylamide A solution of (E)-3-(5-bromo-2-methoxy-phenyl)-acrylic acid (0.072 g, 0.28 mmol) in DMF (10 ml) is treated with 2-(1H benzotriazol-1-yl)-1,1,3,3,-tetramethyluronium tetrafluoroborate (0.09 g, 0.28 mmol) and diisopropylethylamine (0.058 ml, 0.33 mmol). The resultant solution is added to 2-[4-(4-fluoro-benzyl)-piperidin-1-yl]-ethylamine and the mixture stirred at RT for 18 hours. The solvents are evaporated and the crude residue purified by preparative HPLC to afford (E)-3-(5-bromo-2-methoxy-phenyl)-N-{2-[4-(4-fluoro-benzyl)-piperidin-1-yl]-ethyl}-acrylamide [MH]$^+$ 475.2

The following examples were prepared by the methods indicated:

EXAMPLE 4

Method B (E)-3-(5-Cyano-2-methoxy-phenyl)-N-{(S)-2-[4-(4-fluoro-benzyl)-piperidin-1-yl]-1-hydroxymethyl-ethyl}-acrylaniide [MH]$^+$ 451.9

EXAMPLE 5

Method C (E)-N-{2-[4-(4-Cloro-benzyl)-pipelidin-1-yl]-ethyl)}-3-(5-cyano-2-methoxy-phenyl)-acrylamide [MH]$^+$ 422.2

EXAMPLE 6

Method C (E)-3-(5-Cyano-2-methoxy-phenyl)-N-{2-[4-(4-fluoro-benzyl)-piperidin-1-yl]-ethyl}-acrylamide [MH]$^+$ 438.2

EXAMPLE 7

Method C (E)-N-[2-(4-Benzyl-piperidin-1-yl)-ethyl]-3-(5-bromo-2-ethoxy-phenyl)-acrylamide [MH]$^+$ 471.0, 473.8.

The invention claimed is:
1. A compound of formula I,

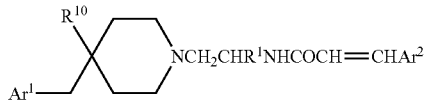

in which
Ar$^1$ is unsubstituted phenyl or phenyl substituted by one or more halogen atoms;
Ar$^2$ is unsubstituted phenyl or phenyl substituted by one or more substituents selected from the group consisting of halogen, cyano or C$_1$-C$_8$-alkoxy;

R$^1$ is hydrogen or methyl optionally substituted by hydroxy;
R$^{10}$ is hydrogen or hydroxy;
and pharmaceutically acceptable salts thereof.

2. A compound according to claim 1, in which Ar$^2$ represents disubstituted phenyl.

3. A compound according to claim 1, in which Ar$^2$ represents phenyl substituted by two halogen substituents (same or different halogen), two C$_1$-C$_4$-alkoxy groups, one halogen and one cyano, one halogen and one C$_1$-C$_4$-alkoxy, or one cyano and one C$_1$-C$_4$-alkoxy.

4. A compound according to claim 1, in which Ar$^1$ is substituted by one halogen substituent para to the indicated methylene group.

5. A compound according to claim 1, which is
(E)-3-(5-Broomo-2-methoxy-phenyl)-N-{2-[4-(4-fluoro-benzyl)-4-hydroxy-piperidin-1-yl]-ethyl}-acrylamide;
(E)-3-(5-Cyano-2-methoxy-phenyl)-N-{(S)-2-[4-(4-chloro-benzyl)-piperidin-1-yl]-1-hydroxymethyl-ethyl}-acrylamide;
(E)-3-(5-bromo-2-methoxy-phenyl)-N-{2-[4-(4-fluoro-benzyl)-piperidin-1-yl]-ethyl}-acrylamide;
(E)-3-(5-Cyano-2-methoxy-phenyl)-N-{(S)-2-[4-(4-fluoro-benzyl)-piperidin-1-yl]-1-hydroxymethyl-ethyl}-acrylamide;
(E)-N-{2-[4-(4-Chloro-benzyl)-piperidin-1-yl]-ethyl}-3-(5-cyano-2-methoxy-phenyl)-acryl
(E)-3-(5-Cyano-2-methoxy-phenyl)-N-{2-[4-(4-fluro-benzyl)-piperidin-1-yl]-ethyl}-acrylamide;
(E)-N-[2-(4-Benzyl-piperidin-1-yl)-ethyl]-3-(5-bromo-2-ethoxy-pheflyl)-acrylamide;
or a pharmaceutically acceptable salt thereof.

6. A pharmaceutical composition comprising as active ingredient a compound according to claim 3, optionally together with a pharmaceutically acceptable diluent or carrier therefor.

7. A process for the preparation of compounds of formula I as defined in claim 1 or pharmaceutically acceptable salts thereof, which comprises the steps of:
(i) (A) for the preparation of compounds of formula I wherein R$^{10}$ represents OH, reacting a compound of formula II

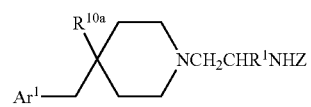

where Ar$^1$ and R$^1$ are as defined in claim 1, R$^{10a}$ represents and Z denotes a solid phase substrate chemically linked to the indicated nitrogen atom with a compound of formula III

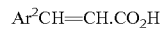

or an amide forming derivative thereof, in which Ar$^2$ is as defined in claim 1, and detaching the resulting product from the substrate to replace Z by hydrogen; or
(B) for the preparation of compounds of formula I wherein R$^{10}$ represents hydrogen, reacting a compound of formula IV

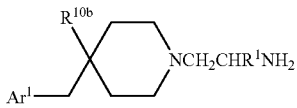

where $Ar^1$, $Ar^2$ and $R^1$ are as defined in claim 1 and $R^{10b}$ represents hydrogen, with a compound of formula III, in which $Ar^2$ is as defined in claim 1 or an amide forming derivative thereof, and (ii) where desired or necessary, converting the resulting salt into the compound of formula I or vice versa.

8. A pharmaceutical composition comprising as active ingredient a compound according to claim 1, optionally together with a pharmaceutically acceptable diluent or carrier therefor.

9. A pharmaceutical composition comprising as active ingredient a compound according to claim 4, optionally together with a pharmaceutically acceptable diluent or carrier therefor.

10. A pharmaceutical composition comprising as active ingredient a compound according to claim 5, optionally together with a pharmaceutically acceptable diluent or carrier therefor.

11. A method of treating an inflammatory or allergic condition, particularly an inflammatory or obstructive airways disease, in a subject in need of such treatment, which comprises administering to said subject an effective amount of a compound of formula I as defined in claim 1 in free form or in the form of a pharmaceutically acceptable salt.

12. A method of treating an inflammatory or allergic condition, particularly an inflammatory or obstructive airways disease, in a subject in need of such treatment, which comprises administering to said subject an effective amount of a compound of formula I as defined in claim 3 in free form or in the form of a pharmaceutically acceptable salt.

13. A method of treating an inflammatory or allergic condition, particularly an inflammatory or obstructive airways disease, in a subject in need of such treatment, which comprises administering to said subject an effective amount of a compound of formula I as defined in claim 4 in free form or in the form of a pharmaceutically acceptable salt.

14. A method of treating an inflammatory or allergic condition, particularly an inflammatory or obstructive airways disease, in a subject in need of such treatment, which comprises administering to said subject an effective amount of a compound of formula I as defined in claim 5 in free form or in the form of a pharmaceutically acceptable salt.

* * * * *